United States Patent [19]

Trotel

[11] Patent Number: 4,964,151
[45] Date of Patent: Oct. 16, 1990

[54] ISOCENTRIC RADIOLOGY STAND

[75] Inventor: Jacques Trotel, Palaiseau, France

[73] Assignee: General Electric CGR SA, Paris, France

[21] Appl. No.: 291,154

[22] Filed: Dec. 28, 1988

[30] Foreign Application Priority Data

Dec. 29, 1987 [FR] France ................................. 87 18300

[51] Int. Cl.⁵ .............................................. H05G 1/02
[52] U.S. Cl. .................................... 378/198; 378/193; 378/197
[58] Field of Search ............... 378/193, 195, 196, 197, 378/198

[56] References Cited

U.S. PATENT DOCUMENTS 3,770,955  11/1973  Tomita et al. ........................ 378/197
3,892,967   7/1975  Grady et al. ......................... 378/197
4,223,230   9/1980  Waerve et al. ...................... 378/198
4,716,581  12/1987  Barud .................................. 378/198

FOREIGN PATENT DOCUMENTS 160749  11/1985  European Pat. Off. .
426094   6/1967  Switzerland .

Primary Examiner—Constantine Hannaher
Assistant Examiner—David P. Porta
Attorney, Agent, or Firm—Oblon, Fisher, McClelland, Maier & Neustadt

[57] ABSTRACT

The invention concerns an X-ray stand permitting isocentric movements and intended particularly for radio diagnosis. Stand includes a base supporting a binding clip having a first and second arm supporting respectively an X-ray source and receiver. According to a feature of the invention, binding clip includes a foot by which it is supported by the base by means of devices to move foot in a circular movement centered on an isocenter point.

7 Claims, 4 Drawing Sheets

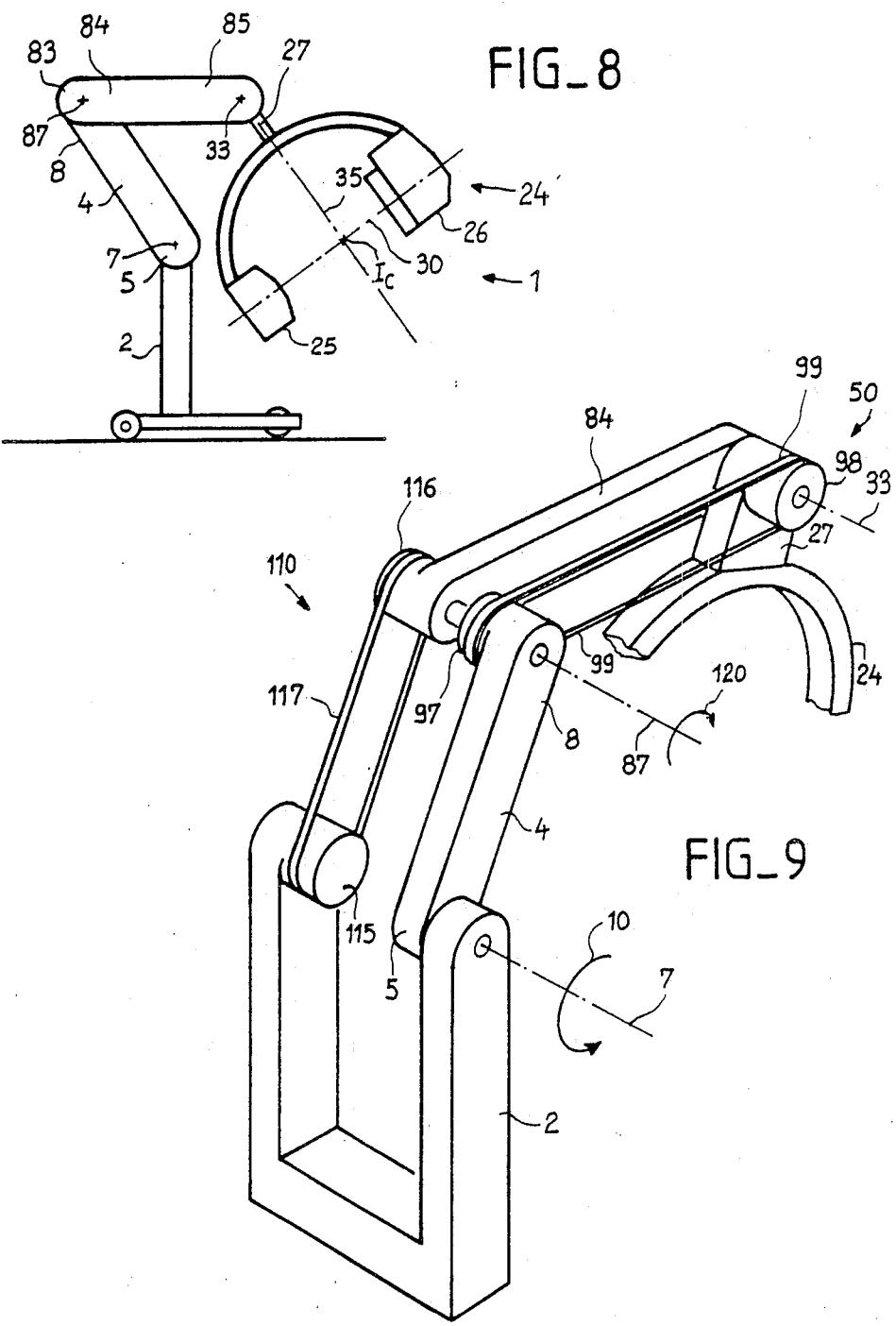

ISOCENTRIC RADIOLOGY STAND

BACKGROUND OF THE INVENTION

1. Field of the Invention

The present invention relates to a radiology stand, particularly intended for radio diagnosis and which permits isocentric exploration or examination of a patient with a multitude of angles.

2. Description of the Prior Arts

Radiological examination of a patient is accomplished by means of an image chain which generally consists essentially of an X-ray source, a collimator, an anti-diffusion grid and an image receiver, supported by the stand and rigidly interconnected together, said X-ray source and collimator being on the same side of the patient to be examined while the anti-diffusion grid and the same image receiver are on the other side. A straight line passing through the center of the X-ray source and the center of the image receiver represents the X-ray axis or the image chain axis which during examination or isocentric exploration, always passes through the area to be analyzed at the same point whatever the orientation of this axis which constitutes the isocenter; the movement by which the orientation of the image chain can be varied while maintaining a fixed position with respect to the isocenter which referred to as the isocentric movement.

The stands which make this isocentric movement possible generally include an open arc curved support, one end of which supports an X-ray source while the other bears an image receiver. The image chain axis formed between the image receiver and the X-ray source passes through the isocenter, said isocenter forming the center of the arc or being on the same axis as the center of the arc in such a way that an isocentric movement is obtained by turning the arc about itself within its own plane around its center, while the arc is made to slide within a sleeve in the form of a semi-circular arc, for instance.

A similar arrangement is used both for large and extensive X-ray systems in which the arc movements are motor-driven as in the case of small X-ray systems such as mobile surgical units or mammaliographs for instance in which the image chain is not excessively heavy so that the arc movements need not be motor-driven; these movements can be obtained by simple manual action by the operator.

In addition, it will be observed that these different radiology stands also permit another isocentric movement which consists of the rotation of the arc plane about a second axis rotation perpendicular to the first, also passing through the isocenter.

One of the drawbacks inherent in such an arrangement is that when the axis of the image chain is parallel to this second axis, there is no modification in its angle of incidence due to the second isocentric movement, i.e. when the arc plane is made to rotate about the second axis of rotation.

Another drawback of this arrangement, particularly for smaller systems without the benefit of motor-drive such as in the case of mobile surgical units, for instance, is that arc movements due to simple manual action by the operator can only be obtained by the rebalancing of the system, that is by placing counterweights outside the system rendering such systems particularly bulky. To underscore the extent of this problem, it will be noted that in some such small systems with the arc moved under manual action, the source of X-rays and the image chain receiver are each supported at the opposite end of the arc at positions well outside said arc i.e. such that the axis of the image chain is no longer on a diameter of the arc. This provides a solution to the problem of balancing but has the drawback of using a supplementary translation movement on each new angle of incidence obtained by the angle of the arc so that the axis of the image chain passes through the isocenter.

It will also be observed that another drawback of these isocentric stands is that it is necessary to add substantial and bulky resources to them, first to substitute the source and the X-ray receiver for one orientation of the image chain axis.

SUMMARY OF THE INVENTION

The present invention relates to a radiology stand which permits isocentric movements and which is free of the aforementioned drawbacks.

According to the invention, a radiology stand comprising a base, a binding clip with two arms, these first and second members bearing respectively a source and an X-ray receiver, with said source and X-ray receiver defining with respect to one another an image chain axis passing through a isocenter and characterized in that said binding clip includes a foot and in that the foot is supported by the base through means of moving the foot in a circular movement centered upon the isocenter.

BRIEF DESCRIPTION OF THE DRAWINGS

Understanding of the invention will be gained from the description which follows, given as a non-limitative example, and the two attached figures among which:

FIG. 8 is a schematic view of a third embodiment of a stand according to the invention; and FIG. 9 is a schematic view of a device designed to keep an arm as disclosed in FIG. 8 at a constant orientation;

DESCRIPTION OF THE PREFERRED EMBODIMENTS

Figure 1:
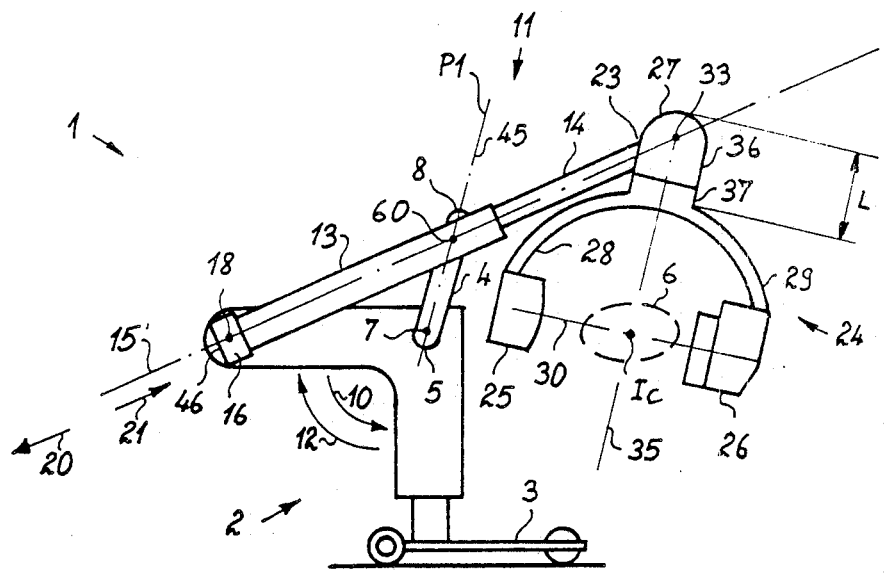
FIGS. 1 to 3 are schematic views of a first embodiment of a radiology stand according to the invention.

FIG. 1 represents a radiology stand 1 in accordance with the first embodiment of the invention which uses a principle of similarity. Radiology stand 1 includes a base 2. In the non-limitative example described herein, base 2 is mounted on a carriage 3. A connecting rod 4 is mounted on base 2 by an end 5 of connecting rod 4 so that connecting rod 4 is free to rotate with respect to base 2 about an axis of rotation 7 (perpendicular to the plane of the figure) whereby the end 5 is attached to base 2. The second end 8 of connecting rod 4 can rotate about axis of rotation 7, circular movement in either of the directions being represented by a first and second arrow 10 and 12. The second end 8 of connecting rod 4 is attached to a telescopic column 11. In the non-limitative example described, telescopic column 11 is formed by arms 13 and 14 which can be displaced with respect to one another in translation along a longitudinal axis 15 of telescopic column 11. Base 2 includes a sleeve 16 into which the first arm 13 of telescopic column 11 is engaged and can slide. The second end 8 of connecting rod 4 is attached to the first arm 13 and is free to rotate with respect to the latter in order to permit at the same time a circular movement of connecting rod 4 about axis of rotation 7. Circular movement of first arm 13 about second axis of rotation 18 (perpendicular to the plane of the figure), passing approximately through the center of sleeve 16 which circular movement of first arm 13 about the second axis of rotation 18, is combined with a movement within sleeve 16 of the first arm 13, in either of the directions shown by the third and fourth arrows 20 and 21 (with respect to the longitudinal axis 15). The movements accomplished by the first arm 13 are also accomplished by the second arm 14 which also moves with respect to the first arm 13 along longitudinal axis 15 and in a same direction 20 and 21 as the first arm 13.

One end 23 of the second arm 14 opposite the first arm 13 bears a 3inding clip 24 which itself also bears an X-ray source 25 and receiver 26; source 25 and receiver 26 are located either side of the patient 6 to be examined. In the non-limitative example described the binding clip 24 is in the form of a tuning fork having one foot 27 and two arms 28, 29, the first arm 28 of which supports the source 25 and the second 29 supports receiver 26. X-ray source and receiver 25, 26 define between one another in a conventional manner an image chain axis 30. Image chain axis 30 passes through a point IC forming the isocenter.

Foot 27 is attached to end 23 of second arm 14 in such a way as to be free to rotate with respect to the latter or, more specifically, with respect to a third axis of rotation 33, perpendicular to the plane containing both arms 28, 29 and the plane of the figure.

In the non-limitative example described hereinafter, foot 27 has length L between end 23 of second arm 14 and the two arms 28, 29, which L length is arranged more or less according to axis 35 forming a fourth axis of rotation 35 passing through isocenter 33. Indeed, in the non-limitative example described hereinafter, foot 27 of binding clip 24 includes a first and second part 36, 37 connected together by conventional bearing means (not shown) so that second part 37 attached to both arms 28, 29 can turn about the fourth axis of rotation 33 with respect to the first part 36 attached to end 23 of the second arm 14. In this configuration, the circular movement of the second end 8 of the connecting rod 4 about the first axis of rotation 7 is transformed into a circular movement of foot 27 about a center formed by isocenter IC.

X-ray stand 1 also includes a device (not shown in the FIG. 1) to orient binding clip 24 according to the orientation of connecting rod 4 i.e., in such a way that on the one hand the attaching point of foot 27 on second arm 14 (attaching point shown by the third axis of rotation 33), and on the other hand isocenter IC can be deduced respectively from end 8 of connecting rod 4 or more specifically from an attaching point 60 of the latter on first arm 13 and from the first axis of rotation 7. In the example of this first embodiment of the invention, this arrangement is obtained by similarities centered on the second axis of rotation 18 whereby the similarity ratio is, for instance, 2.

FIG. 1 represents stand 1 with connecting rod 4 in its first position P1 with connecting rod 4 then lifted, said position P1 being one and the same with the second longitudinal axis of connecting rod 4. With connecting rod 4 in this initial position P1, telescopic column 11 is in an end of travel position i.e., one end 46 of the first arm 13 is more or less level with sleeve 16. In addition, binding clip 24 is turned so that the axis of the image chain 30 and connecting rod 4 preserve the same relative orientations so that axis 30 of the image chain always passes through isocenter IC whereby connecting rod 4 is perpendicular to the axis of image chain 30 in the non-limitative example describe herein.

Figure 2:
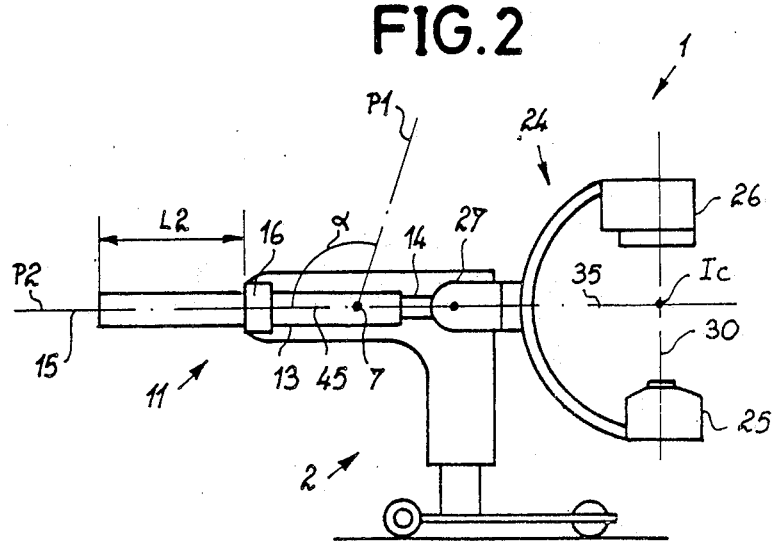

FIG. 2 shows stand 1 complying with the first embodiment of the invention in a second position P2 with connecting rod 4 in a more or less horizontal position, following circular movement of said connecting rod about the first axis of rotation 7 in the direction of the first arrow 10 according to an angle slightly greater than 90°. In a non-limitative example described here, connecting rod 4 is no longer visible in FIG. 2 because it is mounted in a deeper plane than the plane of telescopic column 11 with respect to the plane of the figure and is masked by telescopic column 11 which is also horizontal, and the two longitudinal axes 15, 45 appear one and the same. Telescopic column 11 is then engaged fully in sleeve 16, i.e. end 46 of the first arm 13 protrudes from sleeve 16 by a second maximum length L2. Axis 30 of the image chain always passes through isocenter IC but its orientation, now vertical, is modified by the same amount as the orientation of connecting rod 4.

Figure 3:
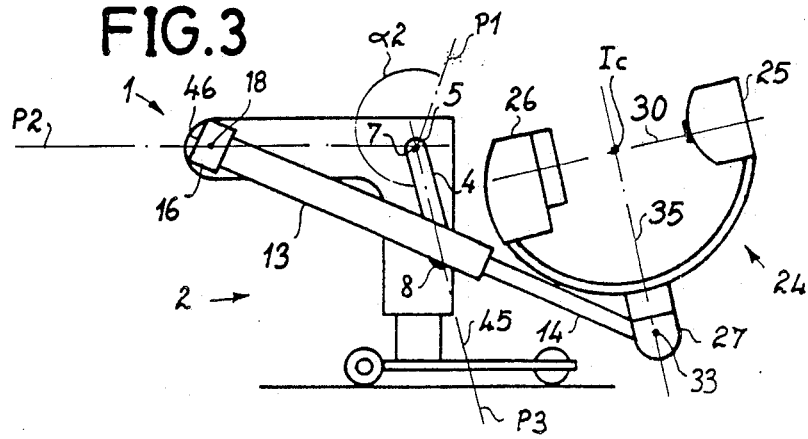

FIG. 3 shows stand 1 of the first embodiment for a third position P3 of connecting rod 4, obtained by continuing the circular movement of the latter in the direction of arrow 10; telescopic column 11 is then again in an end of travel position, i.e. end 46 of first arm 13 has returned to the level of sleeve 16. Between the first position P1 according to the situation shown in FIG. 1, and the third position P3 according to that shown in FIG. 3, the orientation of connecting rod 4 has been modified by an angle 2 greater than 180° and the orientation of the image chain axis 30 has been modified in the same direction and by the same amount. But this illustrates one of the advantages of the invention which is to be able to replace by one another the X-ray source and receiver 25, 26 by simple rotation of connecting rod 4 through 180°. It might also be observed that for all possible positions between positions P1 and P3, orientation of image chain axis 30 could be modified by turning the two arms 28, 29 about a fourth axis of rotation 35.

Figure 4:
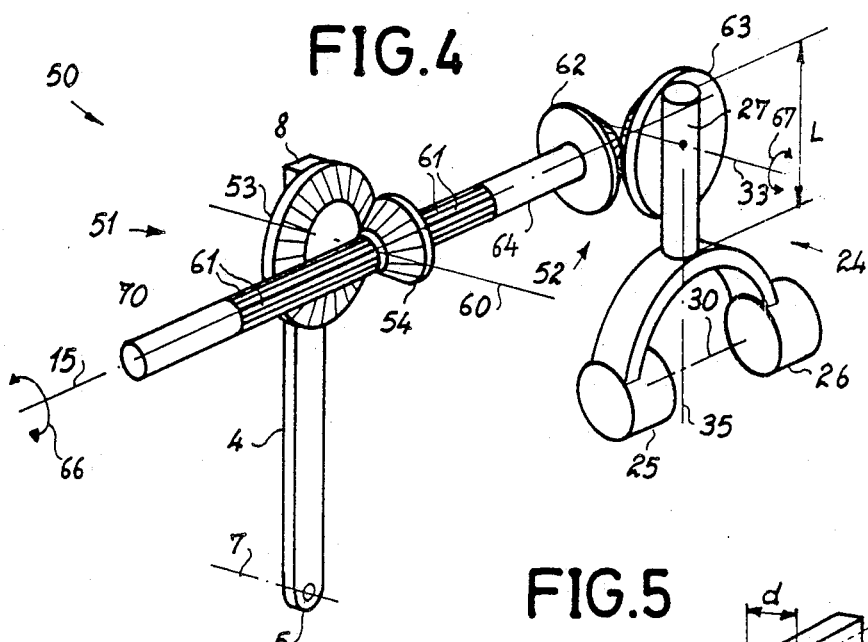
FIG. 4 is a schematic view of a binding clip orientation device as disclosed in FIGS. 1, to 3.

FIG. 4 is a schematic view of device 50 designed to obtained the orientation of binding clip 24. In the non-limitative example described herein, orientation device 50 includes a first and second gear 51, 52 mounted respectively at the second end 8 of connecting rod 4 and at the end of foot 27, as disclosed in FIG. 4. First gear 51 includes a first and second taper pinion 53, 54. The first pinion 53 is mounted at the end 8 of connecting rod 4 and the second pinion 54 on a supporting pin 64 linked with the second arm 14 (not shown in FIG. 4). The second pinion 54 can slide on the supporting pin 64 along the longitudinal axis 15; supporting pin 64 includes for this purpose, ribs 61 parallel to longitudinal axis 15. This arrangement means that second arm 14 can slide with respect to the first arm 13 while maintaining the second pinion 54 in contact with the first pinion 53.

The second gear 52 comprises a third taper pinion 62 mounted at the end of supporting pin 64 and this third pinion 62, meshes with a fourth pinion 63 mounted on foot 27. As shown in FIG. 4, gears 51, 25 are mounted in such a way that in the aforementioned combined movements of the first and second arms 13, 14 and of connecting rod 4, first the second pinion 54 slides along rib 61 and turns on the first pinion 53 about a center according to the attaching axis 60 (whereby the second end 8 of connecting rod 4 is attached to telescopic column 11); this latter movement of second pinion 54 drives supporting pin 64 in rotation about itself, as shown by arrow 56. Further, the latter rotation of supporting pin 64 drives the third pinion 62 to rotate causing it to initiate the rotation of fourth pinion 63 and consequently that of foot 27 about the third axis of rotation 33 as shown by arrow 67; in this way, length L of foot 27 and the fifth axis of rotation 35 are always approximately parallel to connecting rod 4.

Figure 5:
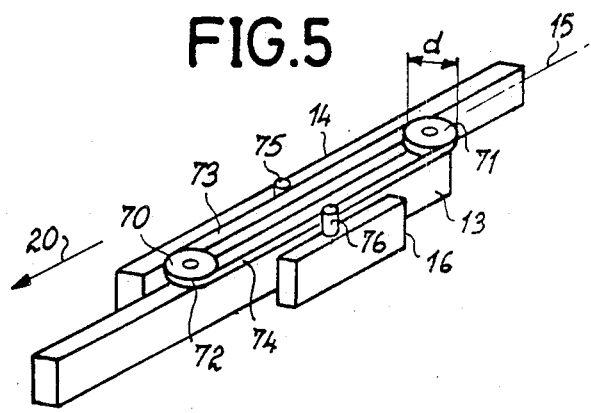
FIG. 5 is a schematic view of a device which provides relative translation movement between two arms designed to carry the binding clips in the first embodiment of the invention.

FIG. 5 discloses schematically as a non-limitative example how the first and second arms 13, 14 are linked with one another to obtain their relative movement and constitute telelscopic column 11. The first arm 13 bears the first and second pulley 70, 71 arranged along longitudinal axis 15 and mounted free to rotate with respect to first shaft 13. Both pulleys 70, 71 are connected by belt 70 which closes about said two pulleys; in this way, between both pulleys 70, 71, belt 72 has a first and second rectilinear section 73, 74 parallel to longitudinal axis 15 and separated from one another by the diameter D of a pulley. The first rectilinear section 73 is integral with a dowel 75 attached to second bar 14 and the second rectilinear part 74 is integral with a second dowel 76 itself integral with a fixed part representing sleeve 16. In this manner, movement of the third arm 13 with respect to sleeve 16, for instance in the direction of the third arrow 20, provokes the movement of the second arm 14 with respect to the first arm 13 and in the same direction and with the same amplitude as for the latter, i.e. with double amplitude with respect to sleeve 16.

Figure 6:
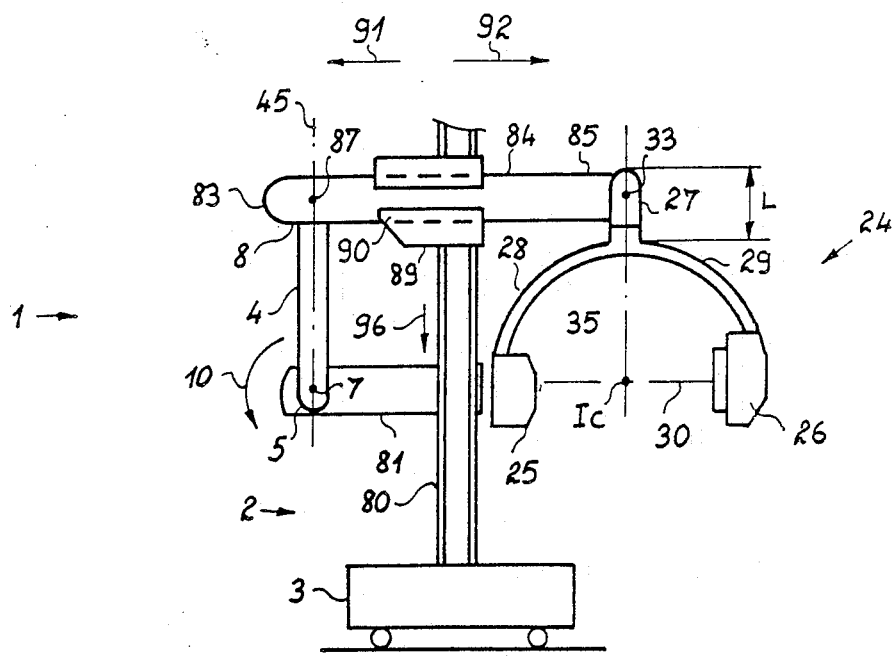
FIG. 6 is a schematic view of a second embodiment of a radiology stand according to the invention.

FIG. 6 gives a non-limitative example of a second embodiment of the X-ray stand 1 in accordance with the invention. Stand 1 includes a column 80. In the non-limitative example of the description, column 80 is vertical and bears a supporting arm 81 itself supporting previously mentioned connecting rod 4. Connecting rod 4 is attached by its end 5 to supporting arm 81 so that it is free to rotate with respect to the latter about the first axis of rotation 7. The second end 8 of connecting rod is attached to an end 83 of a fourth arm 84 whose second 85 bears foot 27 on binding clip 24.

As explained previously, binding clip 24 has a first and second arm 28, 29 supporting respectively the X-ray source and receiver 25, 26 and axis 30 of the image chain passes through isocenter point IC. The second end 8 of connecting rod 4 and the first end 83 of fourth arm 84 are assembled with one another in order to hinge about a fifth axis of rotation 87 perpendicular to the plane of the figure. Foot 27 of binding clip 24 is attached to second end 85 of fourth arm 84 so as to rotate about the third axis of rotation 83 and, as shown in the previous example, the X-ray stand is arranged so that foot 27 and more specifically the third axis of rotation 33, are capable of circular motion according to a circle centered on isocenter IC. For this purpose, the X-ray stand in the second embodiment of the invention includes on the other hand a second carriage 89 moving along column 80 and second sleeve 90 mounted on carriage 89 in which the fourth arm 84 is engaged. The fourth arm 84 is therefore supported by the second sleeve 90 in which it can slide transversely with respect to column 80 in either of the directions depicted by arrows 91, 92. It is observed that firstly, the supporting arm and fourth arm 81, 84 are parallel and that secondly, connecting rod and length L of foot 27 are also parallel so that these components, parallel in pairs, represent a parallelogram and that by maintaining the supporting arm 81 fixed, and deforming the parallelogram, foot 27 is made to rotate about isocenter IC.

Indeed, assuming that fourth arm 84 slides through second arm 90 in the direction of the sixth arrow 91, for example, this movement will cause connecting rod 4 to rotate about the first axis of rotation 7 in the direction of the first arrow 10 and at the same time, will cause carriage 89 to move along column 80 in the direction of an eight arrow 96.

Thus, it is possible to modify the orientation of axis 30 of the image chain as extensively as in the preceding example and it will be observed that this embodiment of the invention is particularly suitable for the balancing of the different movements.

Of course, the rotation of foot 27 about isocenter IC must be accompanied by the orientation of binding clip 24 so that the length L is always more or less parallel to connecting rod 4. This can be obtained by an orientation device 50 (not visible in FIG. 5) which, in this embodiment of the invention, is particularly simple.

Figure 7:
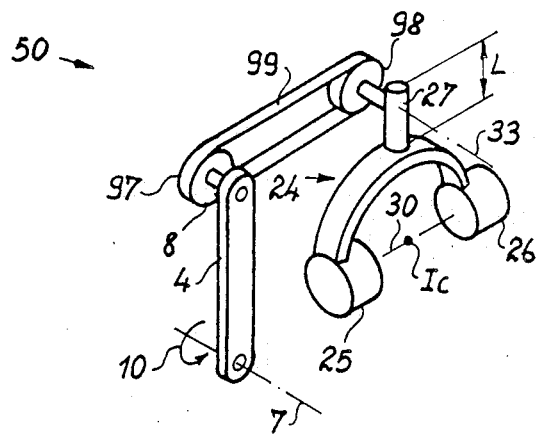
FIG. 7 is a schematic view of a second orientation device for the binding clip.

FIG. 7 demonstrates schematically and as non-limitative example, an achievement using device 50 to orient binding clip 24 within the framework of the second embodiment of the invention depicted by FIG. 6.

The second end 8 of connecting rod 4 depicts a first gear 97 and foot 27 bears a second wheel 98. The two gears are connected together by a toothed belt 99, for instance, which is parallel between the two gears 97, 98 to a fourth arm (84) (shown in FIG. 6). The rotation of connecting rod 4 about the first axis of rotation 7 for instance in the direction shown by first arrow 10, forces the belt 99 to move and the foot 27 to rotate about the third axis of rotation 33; the rotational movements of connecting rod 4 and foot 27 are in the same direction and to the same amplitude so that length L of foot 27 remains parallel to connecting rod 4. As a non-limitative example, FIG. 8 discloses a third embodiment of the X-ray stand 1 according to the invention.

Connecting rod 4 is supported by base 2 to which it is attached by its end 5 so as to be free to rotate about the first axis of rotation 7. The second end 8 of connecting rod 4 can then describe a circular movement about the first axis of rotation 7 as in the previous examples; this circular motion is transmitted to foot 27 of binding clip 24 in the same way as in the second embodiment described with reference to FIG. 6, i.e. by means of the fourth arm 84. For this purpose, the second end 8 of connecting rod 4 is attached to end 83 of fourth arm 84 the second end 85 of which supports foot 27 of binding clip 24.

As long as binding clip 24 is adjusted, and as long as the orientation of the fourth arm 84 is maintained constant with respect to base 2 for instance (horizontal orientation in the described non-limitative examle), a circular movement of the first connecting rod 4 about the first axis of rotation 7 in the direction of the first arrow 10 for instance, will generate circular motion of binding clip 24 on a circle centered on isocenter IC.

Thus, the orientation of axis 30 of the image chain can be modified to the same extent as in the preceding examples.

FIG. 9 is a perspective view which, as a non-limitative example, demonstrates at the same time an achievement using device 50 orienting binding clip 24 within the framework of the third embodiment of the invention disclosed in FIG. 8, and an achievement using a device 110 designed to maintain the orientation of fourth arm 84 constant.

The first orientation device 50 is of the same type as described with reference to FIG. 7. The first connecting rod 4 is attached by its first end 5 to base 2 so as to be free to rotate about the first axis of rotation 7. The second end 8 of the connecting rod bears first gear 97 and foot 27 of binding clip 24 (not partially) bears second gear 98. Both gears are connected together by belt 99. Rotation of connecting rod 4 about the first axis of rotation 7, in the direction shown by the arrow 10 for instance, causes belt 99 to move and foot 27 to rotate about the third axis 33, causing binding clip 24 to assume a suitable orientation. The second orientation device 110 is designed to maintain a constant orientation at second arm 84 and consists of a third and fourth pulley 115, 116 connected together by a second belt 117. The third and fourth pulleys 115, 116 are shown respectivley on base 2 and on the first end 83 of fourth arm 84 so that second belt 117 is tensioned between these two pulleys 115, 116 parallel to first connecting rod 4. The rotation of first connecting rod 4 about the first axis of rotation 7 in the direction of the first arrow 10 causes the second belt 117 to move, itself driving the fourth arm 84 to rotate, with respect to the first connecting rod 4, about the fifth axis of rotation 87 on which are assembled the connecting rod and the fourth arm 84. This rotational movement of the fourth arm 84 is made in a direction represented by arrow 120; this directional rotation is appropriate to maintain the orientation of fourth arm 4 in spite of the movements of connecting rod 4. Obviously, numerous modifications and variations of the present invention are possible in light of the above teachings. It is therefore to be understood that within the scope of the appended claims, the invention may be practiced otherwise than as specifically described herein.

What is claimed is :

1. A radiology stand, which comprises:
a base;
a binding clip having first and second arms bearing, respectively, an X-ray source and a receiver, said X-ray source and said receiver defining with respect to one another an image chain axis passing through an isocenter;
a moving foot which connects said binding clip to said base and which includes means centered on said isocenter for generating circular movement of said binding clip;
a telescopic column connected to said moving foot;
a connecting rod having a first end attached to said base and a second end connected to said telescopic column, said connecting rod being rotatable with respect to said base about an axis of rotation located at said first end; and
means for generating circular movement of said moving foot by rotation of said connecting rod about said axis of rotation.

2. A radiology according to claim 1, which comprises means for maintaining a constant relative orientation between said moving foot and said connecting rod.

3. A radiology stand according to claim 2, wherein said moving foot and said connecting rod are parallelly oriented.

4. A radiology stand according to claim 1, wherein said connecting arm is movable about an angle of at least 180° about said axis of rotation.

5. A radiology stand, which comprises:
a base;
a binding clip having first and second arms bearing, respectively, an X-ray source and a receiver, said X-ray source and receiver defining with respect to one another an image chain axis passing through isocenter;
a moving foot which connects said binding clip to said base;
means connected to said moving foot for generating circular movement of said binding clip and which includes a connecting rod having a first end attached to a base and a second end which is free to rotate with respect to said base about an axis of rotation located at said first end;
means for generating circular movement of said moving foot by rotation of said connecting rod about said axis of rotation;
a mobile arm connecting said moving foot to said second end of said connecting rod wherein said mobile arm has a constant orientation with respect to said base.

6. A radiology stand according to claim 5, wherein said mobile arm is mobile in translation about either of two orthogonal axes.

7. A radiology stand according to claim 5, wherein said base comprises a column and a carriage movably mounted on said column and wherein said carriage supports said mobile arm and which comprises means for moving said mobile arm transversely on said column with respect to said carriage.

* * * * *